United States Patent [19]

Plotkin et al.

[11] Patent Number: 4,636,385
[45] Date of Patent: Jan. 13, 1987

[54] VACCINE, METHOD FOR ITS PREPARATION, AND USE THEREOF IN VACCINATING HUMANS AGAINST ROTAVIRUS INFECTION

[75] Inventors: Stanley A. Plotkin, Philadelphia; H. Fred Clark, Wynnwood, both of Pa.

[73] Assignee: The Wistar Institute of Anatomy & Biology, Philadelphia, Pa.

[21] Appl. No.: 702,041
[22] Filed: Feb. 15, 1985
[51] Int. Cl.$^4$ ................... A61K 39/15; A61K 39/225; A61K 39/42
[52] U.S. Cl. ........................................ 424/89
[58] Field of Search ........................................ 424/89

[56] References Cited

U.S. PATENT DOCUMENTS

| | | | |
|---|---|---|---|
| 2,941,925 | 6/1960 | York et al. | 424/89 |
| 3,293,129 | 12/1966 | Baker | 424/89 |
| 3,838,004 | 9/1974 | Mebus et al. | 424/89 |
| 3,869,547 | 3/1975 | Mebus et al. | 424/89 |
| 4,341,763 | 7/1982 | Zygraich et al. | 424/89 |

OTHER PUBLICATIONS

Mebus et al., Can. Vet Jour., vol. 12:69-72 (Mar. 1983) "Cell Culture Propagation of Neonatal Calf Diarrhea (Scours) Virus".
Mebus et al., J.A.V.M.A., vol. 163:880-883 (1973) "Immunity to Neonatal Calf Diarrhea Virus".
Spence et al., Can. J. Microbiol., vol. 24:353-356 (1978) "Comparison of Rotavirus Strains by Hemagglutination Inhibition".
Fauvel et al., Intervirology, vol. 9, 95-105 (1978) "Hemagglutination and Hemagglutination-Inhibition Studies with a Strain of Nebraska Calf Diarrhea Virus".
Murakami et al., Microbiol. Immunol, vol. 25, 1097-1100 (1981) "Neutralizing Patterns of Anti-Bovine Rotavirus (Lincoln) Serum Against Cytopathic Bovine Rotaviruses Isolated from Calves in Japan".
Naik et al., J. Gen. Virol., vol. 59, 427-430 (1982) "The Differentiation of Calf Rotaviruses by Plaque Morphology and Serum Neutralization".
Vesikari et al., Develop. Biol. Standard, vol. 53, 229-236 (1983) "Epidemiologic Background for the Need of Rotavirus Vaccine in Findland, Preliminary Experience of Rit 4237 Strain of Live Attenuated Rotavirus Vaccine in Adults".
Murakami et al., Infec. and Immun., vol. 40, 851-855 (1983) "Serotypes of Rotaviruses Distinguished by Serum Neutralization".
Wyatt et al., J. of Clinical Microbiol., vol. 18, 310-317 (1983) "Direct Isolation in Cell Culture of Human Rotaviruses and Their Characterization into Four Serotypes".
Woode et al., J. of Clin. Microbiol., vol. 18, 358-364 (1983) "Antigenic Relationships Among Some Bovine Rotaviruses Serum Neutralization and Cross-Protection in Gnotobiotic Calves".
Vesikari et al., The Lancet, Oct. 8, 1983, 807-811 "Immunogenicity and Safety of Live Oral Attenuated Bovine Rotavirus Vaccine Strain Rit 4237 in Adults and Young Children".
Offit et al., Infection and Immunity, vol. 42, 293-300 (1983) "Response of Mice to Rotaviruses of Bovine or Primate Origin Assessed by Radioimmunoassay, Radioimmunoprecipitation and Plaque Reduction Neutralization".
Vesikari et al., The Lancet, May 5, 1984 "Protection of Infants Against Rotavirus Diarrhoea by Rit 4237 Attenuated Bovine Rotavirus Strain Vaccine".
Hoshino et al., The Journal of Infectious Diseases, vol. 149 694-702 (May 1984) "Serotypic Similarity and Diversity of Rotaviruses of Mammalian and Avian Origin as Studied by Plaque-Reduction Neutralization".
Bridger et al., J. Gen. Virol., vol. 65, 1151-1158 (1984) "Antigenic and Pathogenic Relationships of Three Bovine Rotaviruses and a Porcine Rotavirus".

*Primary Examiner*—Ronald W. Griffin
*Attorney, Agent, or Firm*—Howson and Howson

[57] ABSTRACT

A live rotavirus vaccine against bovine and human rotaviruses comprising a strain of live bovine rotavirus which does not hemagglutinate primate red blood cells, gives at least about 20 fold higher titers when neutralized with antiserum therefor as compared to heterologous bovine or primate rotaviruses, and has a migration pattern of its RNA genome segments when determined by PAGE substantially as shown by lane WC3 in FIG. 1, the strain of bovine rotavirus having been serially passaged in primate kidney tissue culture a sufficient number of times that when administered to humans the vaccine is immunogenic without causing disease.

17 Claims, 2 Drawing Figures

VACCINE, METHOD FOR ITS PREPARATION, AND USE THEREOF IN VACCINATING HUMANS AGAINST ROTAVIRUS INFECTION

This invention relates to a vaccine for use in vaccinating humans against rotavirus infection, and to methods for producing and using such vaccine.

BACKGROUND OF THE INVENTION

Acute, infectious diarrhea is a leading cause of disease and death in many areas of the world. In developing countries the impact of diarrheal disease is staggering. During a one year period (1977-1978) in Asia, Africa and Latin America it was estimated that three to five billion cases of diarrhea accounted for five to ten million deaths (Walsh, J. A. et al, N. Engl. J. Med. 1979; 301: 967-974).

Since their initial identification, rotaviruses have been shown to be the most important causative agents of acute gastroenteritis requiring hospitalization of infants and young children. Studies in the United States, England, Australia and Japan have demonstrated that 34% to 63% of children hospitalized with acute diarrhea had rotavirus infections. Although comprehensive studies of gastroenteritis in developing countries have only recently been undertaken, it appears that rotavirus is a pathogen of major importance (Offit, P. A. et al., Comp. Ther. 1982 8(8): 21-26).

Rotavirus-induced gastroenteritis is primarily a disease of early childhood, most commonly affecting children between 6 and 24 months of age. The peak prevalence of the disease occurs during the cooler months in temperate climates, and year-round in tropical areas. Rotavirus is transmitted from person to person by fecal-oral route with an incubation period of from one to three days. Unlike infection in the 6-month to 24-month age group, most neonates studied are asymptomatic or have only mild disease. Also, in contrast to the severe disease encountered in young children, most adult infections are mild or asymptomatic because such episodes represent reinfection generally as a result of contact with children known to be excreting rotavirus (Offit, P. A. et al, ibid.).

Rotaviruses have also been demonstrated as a cause of neonatal diarrhea in several animal species including calves, pigs, lambs and mice.

Rotaviruses, whether of bovine or primate origin, are spherical, about 70 nm in diameter, and their name is derived from their distinctive double capsid structure. Their genome is comprised of 11 segments of double-stranded RNA and a RNA polymerase (Rodger, S. M. et al., J. Clin. Microbiol. 1981; 13: 272-278; Verly, E., et al., J. Gen. Virol. 1977; 35: 583-586; Sabara, M., et al., J. of Virol., Dec. 1982, p 813-822; Clarke, Ian N., et al., Infection and Immunity, May 1982, p 492-497; Rodger, S., et al., J. of Virol., June 1979, p 839-846).

Rotaviruses of different species share common antigens capable of showing serological cross reactions. However, there exists evidence of the existence of different serotypes of rotaviruses characterized by specific surface antigens detected most readily in the serum-neutralization (SN) test. For example, an antiserum prepared against a purified virus is known to give a much higher SN titer with the homologous virus than with viruses of heterologus serotype.

Knowledge of the clinical importance of different rotavirus serotypes is presently incomplete, but there is some epidemiologic evidence that cross-immunity between serotypes in man is limited.

Human rotaviruses may be divided into two subgroups based upon differences in certain antigens in the virus core. (Kapikian, A. Z. et al Infect. Immun, 33: 415-425 (1981); Greenberg, H. et al Infec. Immun. 39: 91-99 (1983)). Subgroup 2 has been redundantly shown to be predominant in human disease. However, subgroup 2 is composed of three distinct serotypes, namely types 1, 3 and 4, which are distinguishable by serum neutralization (SN) tests (Wyatt, R. G. et al, J. Clin. Microbiol. 18: 310-317 (1983)). Serotypes 1 and 3 appear to be the most important causes of disease in humans. Studies carried out at the Childrens Hospital of Philadelphia clearly indicated that serotype 3 was the most common cause of rotavirus gastroenteritis during the 1982-83 season. Other isolates so far serotyped are of serotype 1. No serotype 2 rotavirus was observed during the above study; serotype 4 is known worldwide, but from only a few isolates.

Studies of patients who had experienced sequential infections revealed that illness caused by one serotype did not provide protection against illness caused by another serotype (Zissis, G. et al., Lancet, Jan 7, 1978, pp. 38-39).

Belgian workers also recently reported failure in efforts to immunize adult volunteers with bovine strain NCDV rotavirus (Vesikari, T., et al., Devel. Biol. Std. 53: 229-236 (1983)). In these studies only one of twenty volunteers fed with live NCDV rotavirus exhibited a rise in antibody titer detected with enzyme-linked immunosorbent assay (ELISA) to rotavirus. The same investigators then administered live NCDV rotavirus in higher titer ($10^{8.1}$ $TCID_{50}$) to Finnish infants (Vesikari, T. et al., Lancet, Oct. 8, 1983, pp. 807-811). Thirteen of nineteen children and infants previously seronegative by SN test developed an SN antibody rise to the homologous NCDV rotavirus. However, the only children exhibiting an increase in SN antibody titer to human rotaviruses (serotypes 1 or 2) were those who had preexisting SN antibody titers directed against human rotavirus.

BRIEF SUMMARY OF THE INVENTION

It has now been discovered that certain strains of bovine rotavirus, which are sometimes referred to herein as "WC strains", after low passage in cell culture, provide a vaccine which induces an efficient immune response to bovine and human rotaviruses in young children and infants without causing disease. A live virus designated WC3, which is a representative strain of bovine rotavirus useful in providing the novel vaccine of this invention, has been repeatedly isolated from feces of calves located in southeastern Pennsylvania. Other isolates representative of such type strain have been designated WC2, 3, 4, 5, 6, 7, 8, 9 and 10, and are readily distinguishable from other strains of bovine rotavirus, such as the NCDV strain, by their distinctive RNA electropherotype, i.e. the pattern of migration of virion double-stranded RNA segments as detected by polyacrylamide gel electrophoresis (PAGE, Rodger S. M. et al, J. Clin. Microbiol. 6: p. 610-617 (1977)) and their failure to hemagglutinate primate red blood cells. This strain of bovine rotavirus may also be distinguished from other bovine and primate rotaviruses by a serological test, namely, the serum neutralization (SN) test (Matsuno, S., et al, J. Clin. Microbiol. -5: p. 1-4 (1977)), and plaque morphology.

Rotavirus of the WC strain may be propagated in a variety of cell cultures, particularly simian kidney tissue culture, including the established African green monkey kidney (*Cercopithecus aethiops*) cell lines VERO (ATCC CCL 81), MA-104, BSC-1 (ATCC CCL 26) and CV-1 (ATCC CCL 70) as well as primary rhesus monkey (*Macacca mulatta*) kidney cells and the rhesus monkey diploid cell strain FRhL-2 (ATCC CCL 160). In addition the WC strain may be propagated on primary, secondary or tertiary primate kidney cells, such as those of the African green monkey (Cercopithecus aethiops), the rhesus monkey, and cynomolgous monkeys. The term "primate kidney tissue culture" as used in this specification and claims is intended to include primary, secondary and tertiary cell cultures and established cell lines and cell strains.

The live vaccine is intended to be administered in high doses by the oral or nasal route, preferably the former, to infants and young children to whom the risk of rotavirus infection is relatively high. Since the age of greatest risk is generally of from 6 to 30 months, the vaccine should first be administered to children who are no more than about six months old. Multiple oral doses may be given at periodic intervals, e.g. at 3 to 6 week intervals, to increase the immune response.

The concentration of the vaccine required for administration in doses of $10^5$ to $10^8$, preferably $10^7$, plaque forming units (pfu) per ml is readily obtained in simian kidney tissue culture and thus concentration of the live virus of which the vaccine is composed is not required. However, the vaccine may be purified as for example by subjecting it to treatment to remove cellular components, such as cellular proteins and nucleic acid. The vaccine can be rendered storage stable by subjecting it to freeze drying or by freezing the liquid form thereof at $-20°$ C. to $-70°$ C.

DETAILED DESCRIPTION OF THE INVENTION

Isolation of the Rotavirus

Virus isolates of the WC strain may be recovered from the feces of calves located in southeastern Pennsylvania. Different isolates designated WC2 to WC10 have been recovered from such calves, all of which may be used to provide the vaccine of the present invention. However, in order to simplify discussion, the detailed description of the invention to some extent will be in connection with the isolate WC3.

Section of the Rotavirus Strain

As noted previously rotavirus of the WC strain may be recovered from the feces of calves located in southeastern Pennsylvania. However, it is quite conceivable that a bovine rotavirus strain from calves located in other parts of the world may meet the criteria for use in preparing a vaccine according to this invention, namely, those that have the previously described distinctive RNA electropherotype, do not hemagglutinate primate red blood cells, and are distinguishable from other bovine and primate rotaviruses by the serum neutralization test.

The virus strain used in preparing the vaccine of this invention has been compared with two previously characterized bovine rotavirus strains by several parameters and has been shown to be readily distinguishable from each. The viruses compared are Nebraska calf diarrhea virus (NCDV), ATCC VR-452, isolated in Nebraska by Mebus (Mebus, C. A. et al., Canad. Vet. J. 1971, 12: p 69–72), and used as a bovine vaccine (Mebus, C. A. et al., J.A.V.M.A. 1973, 163: p 880 et seq.) and a Canadian bovine virus strain C486, ATCC VR-917, herein designated CBV, isolated by Babiuk in Saskatchewan (Babiuk, L. A., et al., J. Clin. Microbiol. 1977, 6: p 610–617).

Figure 1:
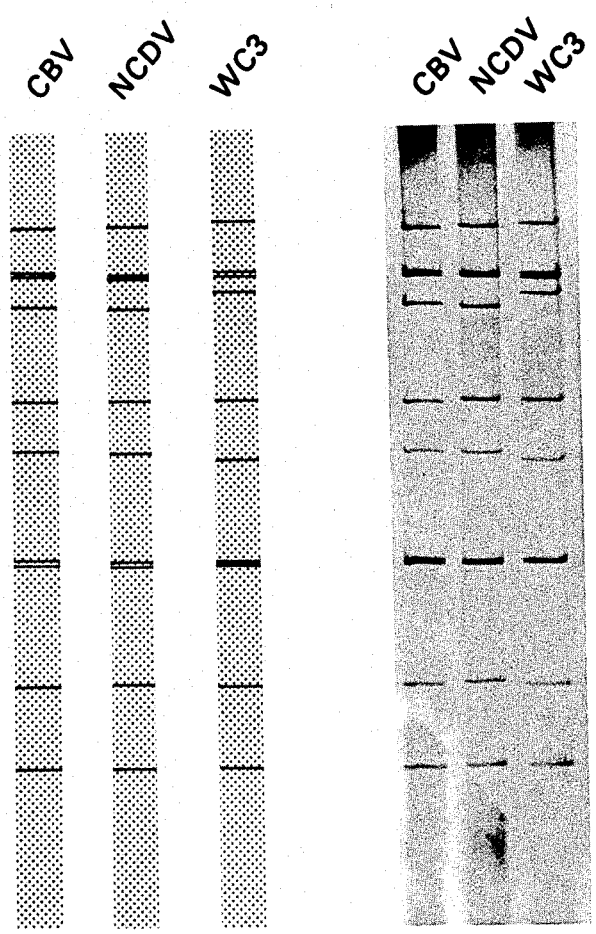

As with human rotaviruses (Rodger, S. M. et al., J. Clin. Microbiol. 1981, 13: p 272–278), bovine rotavirus strains may vary in the characteristic migration patterns of their 11 double-stranded RNA genome segments upon electrophoresis in polyacrylamide gels. A comparison of the RNA migration patterns of the three bovine rotavirus strains, WC3, CBV and NCDV, is shown in FIG. 1. The patterns of strains NCDV and CBV are closely similar and possibly indistinguishable. The WC3 virus strain is clearly distinguishable because of marked differences in the rate of migration of RNA segments 4 and 6 and lesser differences in the migration rate of segment 1, as well as by the separation of segments 2 and 3 and the coincidence of segments 7, 8 and 9.

Both CBV and NCDV are known to agglutinate monkey red blood cells (Spence, L., et al., Canad. J. Microbiol. 1978, 24:353; Fairvel, M. L. et al., Intervirology 1978, 9: p 45–105; Bishai, F. R. et al., Canad. J. Microbiol. 1978, 24 p 1425–1430). A comparison with the WC3 strain is shown in Table 1.

TABLE 1

| Hemagglutination of Rhesus Monkey Red Blood Cells | | |
|---|---|---|
| Rotavirus Strain | Infectious Titer (pfu/ml) | Hemagglutination Titer |
| WC3 | $10^{7.7}$ | <1:2 |
| NCDV | $10^{7.5}$ | 1:256 |
| CBV | $10^{8.5}$ | 1:1024 |

Strain WC3 can be clearly distinguished by its failure to hemagglutinate primate red blood cells.

Figure 2:
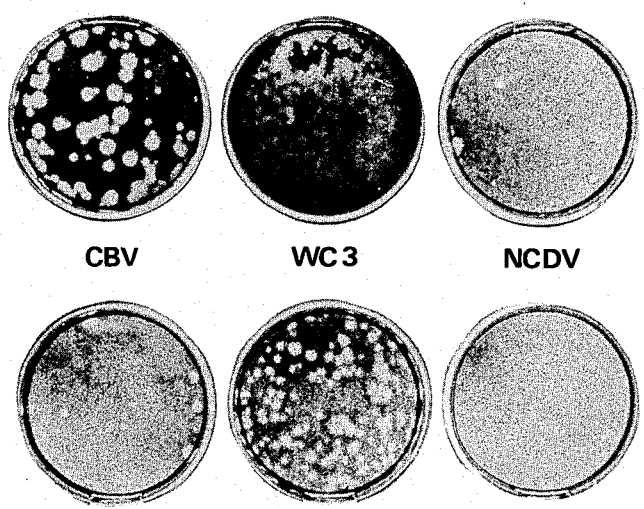

Bovine rotaviruses may differ in their plaque morphology induced in cell culture (Naik et al., J. gen. Virol. 1982, 59: p 427–430). The plaque morphology of strain WC3 compared to strains NCDV and CBV is illustrated in FIG. 2; WC3 virus strain is clearly distinguishable by this test.

Although almost all rotaviruses share group-specific antigens, bovine rotavirus strain NCDV has been distinguished from other rotaviruses of other host species by the serum neutralization test (Hoshino et al., J. Inf. Dis. 1984, 149, 5: p 694–702). Antigenic groups of bovine rotaviruses have not been clearly defined, but the existence of antigenic variation amongst bovine rotavirus strains is known (Fairvel, M. L. et al., ibid; Murakami, Y. et al., Microbiol. Immunol. 1981, 25: p 1097–1100; Woode, G. N. et al., J. Clin. Microbiol. 1983, 18: p. 358–364; Bridger, J. C. et al., J. Gen. Virol. 1984, 65: p 1151–1158; Murakami, Y., et al., Infection and Immunity 1983, 40, 3: p 851–855). A comparison by means of the plaque-reduction serum neutralization test of the WC3 strain with strains NCDV and CBV of bovine rotavirus, Wa strain of human rotavirus (human serotype 1) S2 strain of human rotavirus (serotype 2), ST strain of human rotavirus (serotype 4) and SA11 strain of simian rotavirus (equivalent to human serotype 3) is shown in Table 2. The antisera were prepared in parenterally hyperimmunized guinea pigs or rabbits.

TABLE 2

| Antiserum | Antigenic Relationships (Serum Neutralization Test)* | | | | | | |
|---|---|---|---|---|---|---|---|
| | Rotavirus Strain | | | | | | |
| | WC3 | NCDV | CBV | SA11 | Wa | S2 | ST |
| WC3 (GP R) | 31,250 | 1250 | 1440 | 6250 | 2320 | <250 | <250 |
| NCDV (R101) | 123,250 | 93,750 | 156,250 | 5910 | 2085 | 750 | >6250 |
| CBV (GP Q) | 3910 | 6250 | 25,000 | 2425 | <250 | <250 | 1250 |
| SA11 (R881) | 3200 | 9600 | 8800 | >250,000 | <2000 | | |
| Wa (R192) | 3700 | 3300 | <1250 | 18,250 | >400,000 | | |

*Values are the reciprocal of the highest dilution of serum capable of reducing by 50% the number of plaques in a suspension containing $1 \times 10^3$ pfu/ml of the designated rotavirus.

The results set forth in Table 2 indicate that the WC3 strain of rotavirus, like bovine rotavirus strains NCDV and CBV, is easily distinguished from primate rotavirus strains Wa and SA11. However, the relationship between the different strains of bovine rotaviruses is complex. Antiserum to NCDV crossreacts quantitatively and does not distinguish among the three bovine rotavirus strains WC3, NCDV and CBV. Antiserum to the WC3 strain does selectively neutralize homologous WC3 virus. Antisera to the CBV strain crossreacts less than quantitatively with NCDV and WC3 virus strains (see Table 2). Similar "one way" crossreactions detectable by SN test have previously been reported for bovine rotavirus isolates (Bridger et al., and Murakami et al., 1983, ibid).

The Cell Cultures

As noted above the WC strains of bovine rotavirus can be cultured in primate kidney tissue culture. Preferably the cell lines CV-1 (ATCC CCL-70), BSC-1 (ATCC CCL-26), MA-104 and VERO (ATCC CCL-81) are used alone, or in combination in serial passaging of the virus. When used in combination, a separate but different cell line can be used in each of the various passages.

The primary Cercopithecus kidney cells may be grown in BHK cell medium (MacPherson, I., et al., ibid.), as well as medium 199, in each instance supplemented with 10% fetal bovine serum and 25 μg of gentamicin per ml. The African green monkey kidney cells, CV-1 (ATCC CCL 70), may be grown in BHK cell medium, or medium 199, supplemented with 10% fetal bovine serum and 25 μg of gentamicin per ml. The fetal rhesus monkey cells, MA-104 may be grown in BHK cell medium, supplemented with 10% fetal calf serum, 100 U of penicillin per ml., and 100 μg of streptomycin per ml.

Isolation, Attenuation and Growth of Virus

The WC strain of rotarvirus may be isolated by suspending a fecal sample in Eagles medium containing selected antibiotics, e.g. streptomycin, penicillin, gentamicin and mycostatin. The sample is then centrifuged to remove bacteria and other contaminants.

The suspension from the centrifugation may then be initially isolated on primary African greem monkey kidney cell culture grown in Eagles medium, supplemented with 10% fetal calf serum and containing the sam antibiotics as used to inoculate the medium for the fecal sample. The culture may be maintained at 37° for about 7 days and then frozen at about −70° C. for storage prior to further use.

In preparing the vaccine of this invention, serial infections are performed by sub-inoculation of frozen and thawed whole cell cultures prepared as described into uninfected cell cultures which, as previously noted, may comprise primate kidney tissue culture. Each passage is conducted at 37° C. and continued until clear cytopathic effect (CPE) is evident, which usually occurs 2 to 4 days post inoculation. A total of from $10^5$ to $10^8$ plaque forming units (pfu) per ml. is continously obtained in each passage.

The number of passages may vary from about 5 to about 25, preferably 10 to 20.

In the early passages the substrate cell culture may be grown in Eagles medium, supplemented with 10% fetal calf serum (FCS), 100 μg/ml. of streptomycin and 100 U penicillin. In the later passages the same culture medium may be used except that penicillin is omitted since its presence in the vaccine is undesirable.

Between the initial and later passages it generally is desirable to carry out one or more plaque purification passages, preferably on primate kidney cell culture. Such plaque purification is carried out by first performing a titration of virus by plaque assay method, as for example in MA 104 cells, using agarose overlay as described by Offit et al., J. Virol. Methods 7: 29 (1983). When plaques (areas of dead cells induced by a single infectious unit) are clearly visible, the cells and overlying agarose from a single plaque, well separated from other plaques, are aspirated with a Pasteur pipette and suspended in virus growth medium. Virus in this "plaque-purified" suspension is then further cultivated using the standard technique.

In the final passage primate kidney cells may be grown to confluency in plastic roller bottles containing BHK medium supplemented with 10% neonatal calf serum and 25 μg/ml. of gentamicin. Prior to infection the growth medium is removed and the cells washed with phosphate-buffered saline (PBS) solution. The cells are then infected with the WC virus stock prepared as above (at least 4 passages) at a multiplicity of infection of about 0.1. The culture is maintained at 37° C. for about 60 minutes to permit the virus to attach, and then the inoculum is removed, following which the cultures are fed with BHK medium containing no serum supplement but containing 25 μg/ml. gentamicin and 3 μg/ml. of purified trypsin.

The infected cultures are incubated at 37° C. until CPE is observed, generally within 48 to 96 hours. The cultures are harvested by disrupting the cells by several, usually three, cycles of freezing and thawing followed which cell debris is removed by centrifugation. The supernatant fluid following centrifugation comprises the vaccine which may be stored at −70° C. prior to carrying out tests for sterility and the presence of adventitious viruses.

The vaccine thus prepared is tested for sterility and safety by (1) inoculation of standard medium for growth of bacteria, fungi, and mycoplasma; (2) inoculation of prmiate and human cell culture systems [anti-WC-3 hyperimmune serum is added to cell cultures susceptible to WC3 virus]; and (3) inoculation of adult guinea pigs (IP), adult mice (oral, IC and IV) and newborn mice (oral and IC).

The vaccine may be administered by the oral or nasal route, the dosage generally being on the order of $10^5$ to about $10^8$, preferably $10^7$ pfu.

It has been suggested that the seroconversion rate of the rotavirus vaccine RIT 4237 may be increased by oral administration of the vaccine after milk feeding to neutralize gastric acidity (Vesikari et al, The Lancet, Sept. 22, 1984), p. 700). In order to increase the seroconversion rate of the vaccine of the present invention, it may be combined with a suspension containing 40 mg/cc of magnesium hydroxide and 45 mg/cc of aluminum hydroxide (Maalox ®, William H. Rorer, Inc.). The quantity of the suspension used may be on the order of 1 cc/kilogram body weight.

The safety and efficacy of the vaccine of this invention was demonstrated in a series of tests which are reported in the following examples.

EXAMPLE 1

Preparation of Rotavirus Vaccine

The isolate WC3 was recovered from a calf born in Chester County, Pa. The calf was not permitted to nurse (failure to nurse predisposes to neonatal diarrhea), but transported to the University of Pennsylvania School of Veterinary Medicine when approximately 6 to 10 hours old, and there was fed by hand. At 4 days of age the calf developed diarrhea, and electron microscope (EM) examination of the feces showed the presence of rotavirus.

The fecal sample was suspended in Eagles medium containing 500 µg/ml of streptomycin, 500 U of penicillin, 40 µg/ml. of gentamicin and 50 µg/ml. mycostatin. The sample was centrifuged at 2000×g. for 30 minutes to remove bacteria and other contaminants.

In order to prepare a seed batch of the virus, the supernatant fluid from the centrifuged sample was inoculated onto primary (Cercopithecus) monkey kidney cell culture grown in Eagles medium, supplemented wth 10% fetal calf serum (FCS), and containing the same antibotics as present in the medium into which the fecal sample was inoculated. Prior to infection the cell cultures were washed 2× with phosphate-buffered saline to remove serum (which is inhibiting to rotavirus growth) and then refed with a medium identical to cell growth medium, but containing no serum and containing trypsin (Flow Laboratories) at a concentration of 6.25 µg/ml. The culture was maintained at 37° C. for about 7 days and then frozen at −70° C. for storage for further use. Examination of this culture by immunofluorescent antibody staining for group specific (common) rotavirus antigens (McNulty, M. S., et al, Arch. of Virol. 54: pp 201–209, (1977)) indicated infection of the cells with rotavirus.

Serial infections were then performed by sub-inoculation of frozen and thawed whole cell cultures prepared as above onto uninfected cell cultures. The passage history was as follows: 3 passages in cell line CV1, 2 plaque purifications in cell line MA-104 and 6 passages in cell line CV1.

Each passage was conducted at 37° C. and continued until CPE was evident, usually 2 to 4 days post inoculation. A titer of from $10^7$ to $10^8$ pfu/ml. is routinely obtained in each passage.

In the first 3 passages the cell line CV1 was grown in Eagles medium, supplemented with 10% FCS and 100 µg/ml. streptomycin and 100 U penicillin. In the 2 plaque purification passages employing MA-104 cells, and the subsequent 6 passages in CV 1 cells the same culture medium was used except that penicillin was omitted since its presence in the vaccine is undesirable. Virus-infected cells were maintained in the same medium lacking serum and containing 6.25 µg trypsin/ml. The plaque purification procedure used is as described above.

CV1 cells were grown to confluency in 850 m² plastic roller bottle cultures fed with BHK medium supplemented with 10% neonatal calf serum and 25 µg/ml. of gentamicin. Prior to infection, growth medium was removed and the cell monolayer was washed three times with PBS solution. The cells were then infected wth WC3 virus stock prepared as above (passage 10 to 13) at a multiplicity of infection of approximately 0.1. Virus was allowed to attach for 60 minutes at 37° C. The inoculum was removed and the roller cultures were fed with 80 ml/vessel of BHK medium containing no serum supplement, 25 µg/ml gentamicin, and 3 µg/ml. of purified trypsin (Sigma Chemical Company).

Infected cultures were incubated at 37° C. until confluent cytopathic effect was observed (48 to 96 hours). Then cultures were harvested by disrupting the cells by 3 cycles of freezing and thawing, after which cell debris was removed by centrifugation for 60 minutes at 1800×g. Supernatant fluids following centrifugation were pooled and comprise the vaccine. The vaccine was frozen in bulk at −70° C., pending tests for sterility and freedom from adventitious viruses.

Sterility tests consisted of inoculation of the vaccine into standard laboratory medium for the culture of aerobic and anaerobic bacteria, mycobacteria, and fungi. Testing for mycoplasma was performed by inoculation of cultured mouse (3T3) cells followed by staining by Hoechst stain for intracytoplasmic DNA. Testing for viruses included inoculation of human and primate cell cultures (with specific antiserum to WC3 virus) which were observed for cytopathic effects and/or hemadsorption. Adult mice were inoculated intracerebrally, orally and intravenously. Newborn mice were inoculated intracerebrally and orally, and guinea pigs were inoculated intraperitonealy. Mice were observed for 30 days and guinea pigs for 15 days post inoculation.

Infectious virus content of the vaccine was determined by plaque assay. Final vaccine was prepared by dilution of the vaccine pool to a concentration of $10^7$ pfu/ml. in virus growth medium lacking trypsin, or in PBS.

A deposit of the virus after the seed batch had been cultured twice on uninfected cells of the cell line CV-1 was made with the American Type Culture Collection (ATCC) Rockville, Md., U.S.A. on Feb. 14, 1985 and has been given the accession number ATCC VR-2101. A deposit of the attenuated virus after the 10 th passage according to this example was made with the ATCC on Feb. 14, 1985, accession number ATCC VR-2102. It is to be understood that unless stated to the contrary, all deposits with the ATCC referred to in this application are available to the public upon grant of a patent to the assignee, The Wistar Institute of Anatomy and Biology, Philadelphia, Pa., U.S.A., disclosing them. The deposits are also available as required by international conventions, including the European Patent Convention and the Budapest Tready, and foreign patent laws pertaining to countries where counterparts of this application are filed. The availability of a deposit does not constitute a license to practice the invention of this application in derogation of any patent issued thereon or on any division or continuation of this application.

EXAMPLE 2

Administration of Vaccine to Adults

The vaccine of Example 1 was administered orally in one dose of $10^7$ pfu/ml. to five normal adult human volunteers as a test for safety, immunogenicity and possible shedding of virus into the feces.

All volunteers exhibited no symptoms of clinical illness. Results of studies of virus shedding into stool and of SN tests for antibody to rotavirus are set forth in Table 3. As can be seen by reference to the table, no virus could be detected in stool (by virus isolation attempts) between 1 and 28 days post inoculation. One of the five volunteers (MK-M) exhibited a modest rise in antibody to WC3 in serum at 7 and 14 days after inoculation as determined by the SN test, but not to Wa human rotavirus. The other volunteers did not show increase in antibody to either WC2 of Wa rotarvius in SN antibody determinations.

TABLE 3

| Volunteer | Day | Serum neutralizing Antibody* WC3 | Wa | Virus in Stool |
|---|---|---|---|---|
| GB | 0 | 365 | 140 | none |
|  | 1 |  |  | " |
|  | 2 |  |  | " |
|  | 4 |  |  | " |
|  | 7 | 560 | 325 | " |
|  | 14 | 250 | 135 | " |
|  | 28 | 160 | <50 | " |
| MD | 0 | 85 | 245 | none |
|  | 1 |  |  | " |
|  | 2 |  |  | " |
|  | 4 |  |  | " |
|  | 7 | 145 | 175 | " |
|  | 14 | 75 | 120 | " |
|  | 28 | 85 | 100 | " |
| MK-M | 0 | 40 | 145 | none |
|  | 1 |  |  | " |
|  | 2 |  |  | " |
|  | 4 |  |  | " |
|  | 7 | 105 | <50 | " |
|  | 14 | 230 | <50 | " |
|  | 28 | 70 | <50 | " |
| MK-F | 0 | 105 | 215 | none |
|  | 1 |  |  | " |
|  | 2 |  |  | " |
|  | 4 |  |  | " |
|  | 7 | 105 | 195 | " |
|  | 14 | <50 | 215 | " |
|  | 28 | 50 |  | " |
| DS | 0 | <50 | >1250 | none |
|  | 1 |  |  | " |
|  | 2 |  |  | " |
|  | 4 |  |  | " |
|  | 7 | <50 | >1250 | " |
|  | 14 | <50 | >1250 | " |

TABLE 3-continued

| Volunteer | Day | Serum neutralizing Antibody* WC3 | Wa | Virus in Stool |
|---|---|---|---|---|
|  | 28 | <50 | 1030 | " |

*Units: See footnote to Table 2.

The serum, saliva and stools of the volunteers were subjected to ELISA test and the results obtained are given in Table 4. The ELISA test detects universal group specific rotavirus antigens. Stool and saliva were tested because antibody within the intestinal lumen is believed to be essential for protection against rotaviruses (McNulty, M. S. et al., Vet. Record 1976, 99: 229-230; Snodgrass, D. R. et al., Arch. Virol. 1976, 52: 201-205). Saliva contains predominantly secretory type antibody, the synthesis of which may parallel secretory antibody production in the intestine. As was the case in the serum SN antibody studies, only volunteer MK-M showed a significant increase in serum antibody titer. The significance of high ELISA antibodies found in the serum and stool of volunteer MD on day 14 post inculation only is not known.

TABLE 4

| Vol | Day | Serum IgG 1:100 | Serum IgA 1:20 | Saliva IgG 1:1 | Saliva Sec. IgA 1:1 | Stools IgG 1:100 | Stools Sec. IgA 1:100 |
|---|---|---|---|---|---|---|---|
| GB | 0 | 714 | 228 | 42 | 86 | 43 | 43 |
|  | 7 | 767 | 198 | 19 | 49 |  |  |
|  | 14 | 663 | 208 | 125 | 109 | −6 | 56 |
|  | 28 | 543 | 160 | 2 | 54 |  |  |
| MD | 0 | 515 | 422 | 112 | 106 | 19 | 28 |
|  | 7 | 498 | 404 | 95 | 106 |  |  |
|  | 14 | 672 | 901 | 41 | 105 | 136 | 181 |
|  | 28 | 594 | 532 | 87 | 128 |  |  |
| MK-M | 0 | 138 | 246 | 0 | 44 | 18 | 16 |
|  | 7 | 150 | 257 | 17 | 26 |  |  |
|  | 14 | 511 | 657 | 10 | 67 | 28 | 78 |
|  | 28 | 662 | 605 | 20 | 42 |  |  |
| MK-F | 0 | 529 | 162 | 38 | 54 | 6 | 21 |
|  | 7 | 525 | 187 | 24 | 66 |  |  |
|  | 14 | 491 | 173 |  |  |  |  |
|  | 28 |  |  | 47 | 71 |  |  |
| DA | 0 | 712 | 504 | −6 | 16 | 23 | 43 |
|  | 7 | 765 | 436 | 29 | 54 |  |  |
|  | 14 | 830 | 454 | 9 | 73 | 10 | 20 |
|  | 28 | 731 | 516 | 15 | 56 |  |  |

Values are $OD_{450}(+V) - OD_{450}(-V)$. WC3 virus in wells. Underlined values are > OD (−V) and > day 0 value.

EXAMPLE 3

Oral Inoculation of Children and Infants with Rotavirus Vaccine

Based upon the study indicating clinical safety and lack of fecal shedding in adult volunteers, the oral administration of WC3 vaccine of Example 1 was extended to children and infants. These (and the adult trials) have been approved by the Human Subjects Review Committees of both the Wistar Institute and the Children's Hospital of Philadelphia. Informed consent was obtained from the patient (adult) or responsible parent (child).

Studies of oral vaccination of children and infants were performed in parallel in two clinical populations: (1) private patients of Japanese pediatricians vaccinated under the direction of Dr. Toru Furukawa, Kanazawa Medical University, Ishikawa, -Ken, Japan, and (2) patients at the outpatient public medical clinic of the Children's Hospital of Philadelphia. The vaccine used was that of Example 1 and was the same lot as that previously given to adults.

After explanation of the vaccine procedure to the parents and obtaining informed parental consent, and a determination that the infant/child was clinically well, the following protocol was followed. The child was bled by finger-stick or venipuncture, a rectal swab or stool was obtained, and the child was given an oral dose of 1.0 ml of vaccine mixed with 1.5 ml. of 20% cherry-flavored syrup. The health of the child was monitored by daily telephone contact for seven days after inoculation. On the third day after inoculation a stool sample was obtained to determine whether fecal shedding of virus was occurring. A post-immunization blood sample and stool sample was obtained 28 days after administration of the vaccine. (It has not been possible to obtain fecal samples from all of the Japanese children.)

The WC3 vaccine of Example 1 was first given in a dose of $10^3$ pfu to a six-year old child and next in a dose of $10^5$ pfu to two infants aged 9 months and 5 months. None became ill or shed virus in feces. Therefore a trial of full dose $10^7$ pfu of WC3 vaccine was initiated. The first children given $10^7$ pfu were age 10 years and age 6 years and they remained clinically well. Subsequently a full dose of WC3 vaccine was given to 27 additional children aged from 6 months to 6 years. None exhibited any clinical signs of disease and none excreted detectable levels of virus in feces. The results of serum neutralization (SN) tests of vaccinees for whom these data are completed are listed in Tables 5 and 6. Since applicants and others (Vesikari et al, Lancet 1983, ii, p. 804) have observed a possible inhibiting effect of pre-existing serotype-specifice SN antibody on the active immune response, applicants have separated the data based upon whether or not vaccinees had pre-immunization serum SN antibody to WC3 rotavirus.

The results of WC3 vaccine oral immunization of WC3 seronegative infants and children are listed in Table 5. SN titers were determined based upon 50% plaque-reduction by five-fold serial dilutions of test serum. In this test a three-fold rise in SN titers was considered to be real. Using this criterion, 14 of 16 vaccinees exhibited an SN response to one or more rotavirus serotypes. All seven infants less than 2 years of age exhibited a strong (>5-fold increase) in SN respone to homologous (and other) rotaviruses. A 2 year old and one 35 month old vaccinee did not exhibit an SN response. However, each of two six year olds mounted a strong SN response.

A heterologous SN response to SA 11 (serotype 3) rotavirus was induced in all seven vaccinees less than 2 years old, including three who were previously seropositive to SA 11 virus. Older vaccinees with a >5-fold increase in titer to WC3 virus also exhibited an SN antibody increase to SA 11 virus. Ten vaccinees developed an increase in SN titer to Wa (serotype 1) rotavirus; however only two of these responders were previously seronegative for SN antibody to serotype 1 rotavirus. Two one year old vaccinees were determined to develop an increase in antibody to serotype 2 (strain S2) rotavirus.

The responses to oral administration of WC3 vaccine of Example 1 of five children previously seropositive for SN antibody to this virus are shown in Table 6. A single 10 year old did not respond. Two of four children aged 4 years or less developed increased SN antibody to WC3 virus and SA 11 virus. One of these and one other child exhibited increased SN antibody to Wa rotavirus.

Summary of Studies with Infants and Children

Studies to date indicate that WC3 vaccine of this invention is an effective immunogen capable of inducing SN antibody responses specific for both the immunizing bovine virus and heterologous human rotavirus serotypes. Both the pre-existing specific SN antibody profile and the age of the vaccinee appear to affect the efficiency of immunization. Eight of nine infants less than two years of age exhibited a strong SN antibody response, including seven of seven infants previously seronegative to WC3 virus. Overall, 14 of 16 infants vaccinated and seronegative to WC3 developed an SN antibody response. WC3 vaccine efficiently induced an SN antibody response to SA 11 (serotype 3) rotavirus in vaccinees with or without prior SN antibody to SA 11. WC3 vaccine induced an antibody response to Wa (serotype 1) rotavirus most efficiently in vaccinees with prior antibody to Wa strain rotavirus.

TABLE 5

Response of Children Seronegative for WC3 Inoculated With WC3 Rotavirus Vaccine

| Child | Age | Fecal Shedding | Days P.I. | Serum WC3 | NCDV | Wa | SA11 | S2 | RIP*** Increase |
|---|---|---|---|---|---|---|---|---|---|
| PA10** | 9 mo | — | 0 | 85 | | <50 | <50 | | |
| | | | 28 | 3750 | | <50 | 250 | | |
| PA11 | 9 mo | — | 0 | <50 | | <50 | <50 | | |
| | | | 28 | 250 | | <50 | 175 | | |
| PA8 | 10 mo | — | 0 | <50 | | 165 | 50 | | |
| | | | 28 | 2095 | | 1110 | 1250 | | |
| JA6 | 1 yr | | 0 | <50 | <50 | 250 | 965 | 965 | + |
| | | | 28 | 3350 | 1125 | 4835 | 6250 | 1250 | |
| JA7 | 1 yr | | 0 | <50 | <50 | 50 | 1030 | 135 | ± |
| | | | 28 | 1720 | 525 | 1250 | 6250 | 1250 | |
| JA16 | 1 yr | | 0 | <50 | | 50 | <50 | | |
| | | | 28 | 1250 | | <50 | 180 | | |
| PA12 | 22 mo | — | 0 | <50 | | 925 | 250 | | |
| | | | 28 | 620 | | 5175 | 4720 | | |
| PA9 | 2 yr | — | 0 | <50 | | n.d. | n.d. | | |
| | | | 28 | 85 | | n.d. | n.d. | | |
| JA12 | 2 yr | | 0 | <50 | | 50 | 235 | | |
| | | | 28 | ≦50 | | 155 | 50 | | |

TABLE 5-continued

Response of Children Seronegative for WC3 Inoculated With WC3 Rotavirus Vaccine

| Child | Age | Fecal Shedding | Days P.I. | Serum WC3 | NCDV | Wa | SA11 | S2 | RIP*** Increase |
|---|---|---|---|---|---|---|---|---|---|
| JA14 | 2 yr | | 0 | ≦50 | | 695 | 250 | | |
| | | | 28 | 250 | | 2395 | 3460 | | |
| PA6 | 30 mo | — | 0 | ≦50 | | 715 | <250 | | |
| | | | 28 | 4565 | | >6250 | >1250 | | |
| PA1 | 35 mo | — | 0 | <50 | | 775 | 150 | | |
| | | | 28 | 100 | | 1095 | 175 | | |
| JA8 | 3 yr | | 0 | <50 | 175 | 95 | 160 | | + |
| | | | 28 | 1250 | 1250 | >1250 | >1250 | | |
| JA11 | 5 yr | | 0 | <50 | | <50 | 95 | | |
| | | | 28 | 165 | | <50 | 155 | | |
| JA4 | 6 yr | — | 0 | 50 | <50 | 100 | 900 | | + |
| | | | 28 | 5000 | 1250 | 885 | 20,350 | | |
| JA15 | 6 yr | | 0 | 50 | | 240 | 250 | | |
| | | | 28 | 895 | | 930 | 6250 | | |

*WC3 = bovine rotavirus isolates at Wistar Institute
NCDV = bovine rotavirus "Nebraska calf diarrhea virus"
Wa = human rotavirus - serotype 1
SA11 = simian rotavirus - serotype 3
S2 = human rotavirus - serotype 2
**PA vaccinees were inoculated in Philadelphia, PA
JA vaccinees were inoculated in Japan
***RIP = Radioimmunoprecipitation of rotavirus proteins

TABLE 6

Response of Children Seropositive for WC3 Inoculated with WC3 Rotavirus Vaccine*

| Child | Age | Fecal Shedding | Days P.I. | WC3 | Wa | SA11 |
|---|---|---|---|---|---|---|
| PA2 | 1 yr | — | 0 | 250 | >1250 | 250 |
| | | | 28 | 180 | 2595 | 50 |
| PA3 | 1 yr | — | 0 | 230 | 980 | 150 |
| | | | 28 | 3330 | >6250 | >1250 |
| JA13 | 3 yr | | 0 | 250 | 1250 | 820 |
| | | | 28 | 1005 | 1030 | 2915 |
| PA5 | 4 yr | | 0 | 385 | 365 | 250 |
| | | | 28 | 250 | 1105 | 250 |
| JA1 | 10 yr | — | 0 | 190 | 1050 | 765 |
| | | | 28 | 220 | 1070 | 795 |

*See legend for Table 5

The vaccine of the present invention provides unexpected results as compared to published observations of infants inoculated with the bovine NCDV rotavirus vaccine (Vesikari, T. et al., Lancet Oct. 8, 1983, pp 807–811 and Lancet May 5, 1984, pp 977–980), particularly as regards higher percentages of seroconversion, especially with respect to human rotarviruses.

We claim:

1. A method of producing a live rotavirus vaccine against bovine and human rotaviruses, including human serotype 3, which comprises inoculating onto monkey kidney cell culture a strain of live bovine rotavirus which does not hemagglutinate primate red blood cells, gives at least about 20 fold higher titers when neutralized with antiserum therefor as compared to heterologus bovine and primate rotaviruses, and has a migration pattern for its RNA genome segments when determined by PAGE substantially as shown by lane WC3 in FIG. 1, to prepare a seed batch of said virus strain serially passaging virus from said seed batch on cells of the cell line CV-1 (ATCC CCL 70), subjecting said passaged virus to plaque purification on cells of the cell line MA-104, further passaging said plaque-purified virus on cells of the cell line CV-1 (ATCC CCL 70), and harvesting the resulting vaccine from disrupted cells obtained from said last passage, the total number of passages being from about 5 to about 25 and being such that when administered to humans the vaccine is immunogenic without causing disease.

2. The method according to claim 1 in which said bovine rotavirus is serially passaged from about 10 to about 20 times.

3. The method of claim 1 in which said strain of rotavirus comprises the isolate designated WC3 (ATCC VR 2101).

4. A method of producing a live rotavirus vaccine against bovine and human rotaviruses, including human serotype 3, which when administered to humans is immunogenic without causing disease, which comprises inoculating onto primary Cercopithecus monkey kidney cell culture a strain of live bovine rotavirus which does not hemagglutinate primate red blood cells, gives at least about 20 fold higher titers when neutralized with antiserum therefor as compared to heterologus bovine and primate rotaviruses, and has a migration pattern for its RNA genome segments when determined by PAGE substantially as shown by lane WC3 in FIG. 1, said strain of rotavirus comprising the isolate designated WC 3 (ATCC VR 2101), to prepare a seed batch of said virus strain, serially passaging virus from said seed batch three times on cells of the cell line CV-1 (ATCC CCL 70), subjecting said passaged virus to two successive plaque purifications on cells of the cell line MA-104, further passaging said plaque-purified virus six times on cells of the cell line CV-1 (ATCC CLL 70) and harvesting the resulting vaccine from disrupted cells obtained from the last passage.

5. A live rotavirus vaccine against bovine and human rotaviruses, including human serotype 3, which when administered to humans is immunogenic without causing disease, comprising a strain of live bovine rotavirus which does not hemagglutinate primate red blood cells, gives at least about 20 fold higher titers when neutralized with antiserum therefor as compared to heterologous bovine or primate rotaviruses, and has a migration pattern of its RNA genome segments when determined by PAGE substantially as shown by lane WC3 in FIG. 1, said strain of rotavirus having been inoculated onto monkey kidney cell culture to prepare a seed batch of said virus strain, virus from said seed batch having been serially passaged on cells of cell line CV-1 (ATCC CCL 70), subjected to plaque purification on cells of cell line MA-104, then serially passaged on cells of the cell line CV-1 (ACC CCL 70), the total nunber of passages being from about 5 to about 25, and the resulting vaccine having been harvested from disrupted cells from the last passage.

6. The vaccine according to claim 5 in which said bovine rotavirus is serially passaged from about 10 to about 20 times.

7. The vaccine of claim 5 in which said strain of rotavirus comprises the isolate designated WC3 (ATCC VR-2101).

8. The vaccine according to claim 5 in which said vaccine also contains aluminum and magnesium hydroxides.

9. A method of vaccinating human beings against bovine and human rotavirus infection comprising administering by oral or nasal route to human beings at least one dose comprising from about $10^5$ to about $10^8$ pfu, of the vaccine of claim 5.

10. The method according to claim 9 in which the dose comprises about $10^7$ pfu.

11. A method of vaccinating human beings against bovine and human rotavirus infection comprising administering by oral or nasal route to human beings at least one dose comprising about $10^7$ pfu, of the vaccine of claim 6.

12. The method according to claim 10 in which said dose is administered by the oral route.

13. The method according to claim 9 in which at least one additional dose of said vaccine is administered by oral or nasal route about 3 to 6 weeks after the first dose.

14. A live rotavirus vaccine against bovine and human rotaviruses, including human serotype 3, which when administered to humans is immunogenic without causing disease, comprising a strain of live bovine rotavirus which does not hemagglutinate primate red blood cells, gives at least about 20 fold higher titers when neutralized with antiserum therefor as compared to heterologous bovine or primate rotaviruses, and has a migration pattern of its RNA genome segments when determined by PAGE substantially as shown by lane WC3 in FIG. 1, said strain of rotavirus comprising the isolate designated WC 3 (ATCC VR 2101), and said strain of rotavirus having been inoculated onto primary Cercopithecus kidney cell culture to prepare a seed batch of said virus strain, virus from said seed batch having been serially passaged three times on cells of cell line CV-1 (ATCC CCL 70), subjected to two successive plaque purifications on cells of cell line MA-104, then serially passaged six times on cells of the cell line CV-1 (ACC CCL 70), and the resulting vaccine having been harvested from disrupted cells from the last passage.

15. A method of vaccinating human beings against bovine and human rotavirus infection comprising administering by oral or nasal route to human beings at least one dose comprising about $10^7$ pfu of a live rotavirus vaccine comprising a strain of live rotavirus which does not hemagglutinate primate red blood cells, gives at least about 20 fold higher titers when neutralized with antiserum therefor as compared to heterologous bovine or primate rotaviruses, and has a migration pattern of its RNA genome segments when determined by PAGE substantially as shown by lane WC3 in FIG. 1, said strain of rotavirus comprising the isolate designated WC 3 (ATCC VR 2101), and said strain of rotavirus having been inoculated onto primary Cercopithecus kidney cell culture to prepare a seed batch of said virus strain, virus from said seed batch having been serially passaged three times on cells of cell line CV-1 (ATCC CCL 70), subjected to two successive plaque purifications on cells of cell line MA-104, then serially passaged six times on cells of the cell line CV-1 (ACC CCL 70), and the resulting vaccine having been harvested from disrupted cells from the last passage.

16. The method according to claim 15 in which said vaccine is administered by oral route in combination with an aqueous suspension of aluminum and magnesium hydroxides.

17. The method according to claim 16 in which said suspension contains about 40 mg. of magnesium hydroxide and about 45 mg of aluminum hydroxide per ml., and is administered in the amount of about 1 ml. per kilogram of body weight.

* * * * *